(12) United States Patent
Muscarella

(10) Patent No.: US 10,668,044 B2
(45) Date of Patent: Jun. 2, 2020

(54) BLENDED CANNABIS COMPOUNDS AND METHODS OF MAKING THE SAME

(71) Applicant: William H. Muscarella, Roswell, GA (US)

(72) Inventor: William H. Muscarella, Roswell, GA (US)

( * ) Notice: Subject to any disclaimer, the term of this patent is extended or adjusted under 35 U.S.C. 154(b) by 0 days.

(21) Appl. No.: 15/679,627

(22) Filed: Aug. 17, 2017

(65) Prior Publication Data

US 2018/0369191 A1    Dec. 27, 2018

Related U.S. Application Data

(60) Provisional application No. 62/525,527, filed on Jun. 27, 2017.

(51) Int. Cl.
*A61K 31/352* (2006.01)
*A61K 31/05* (2006.01)

(52) U.S. Cl.
CPC ............ *A61K 31/352* (2013.01); *A61K 31/05* (2013.01); *A61K 2300/00* (2013.01)

(58) Field of Classification Search
CPC .................................................. A61K 31/352
USPC ........................................................ 514/454
See application file for complete search history.

(56) References Cited

U.S. PATENT DOCUMENTS

| 8,753,696 | B1 * | 6/2014 | Lewis ................. A61K 36/185 424/725 |
| 2007/0041994 | A1 * | 2/2007 | McDowell, Jr. ....... A61K 33/04 424/195.15 |
| 2010/0216872 | A1 | 8/2010 | Letzel et al. |
| 2017/0020895 | A1 * | 1/2017 | Gestwicki ............ A61K 31/045 |
| 2017/0157041 | A1 | 6/2017 | Goldner |

FOREIGN PATENT DOCUMENTS

| CA | 3031300 A1 * | 2/2018 | ........... A61K 36/185 |
| CN | 106579402 A | 4/2017 | |
| RU | 2599028 C2 | 10/2016 | |
| WO | WO-2013147965- | * 10/2013 | ........... A61K 31/352 |
| WO | WO-2013147965 A1 | * 10/2013 | ........... A61K 31/352 |
| WO | WO 2017/091764 A1 | 6/2017 | |
| WO | WO-2019087074- | * 5/2019 | ............. A24B 15/00 |

OTHER PUBLICATIONS

Nicholson AN, Turner C, Stone BM, Robson PJ. Effect of Delta-9-tetrahydrocannabinol and cannabidiol on nocturnal sleep and early-morning behavior in young adults. J Clin Psychopharmacol. Jun. 2004;24(3):305-13. PubMed PMID: 15118485. (Year: 2004).*
Nicholson AN, Turner C, Stone BM, Robson PJ. Effect of Delta-9-tetrahydrocannabinol and cannabidiol on nocturnal sleep and early-morning behavior in young adults. J Clin Psychopharmacol. Jun. 2004;24(3):305-13. Pub.*
Nida. Marijuana as Medicine. National Institute on Drug Abuse website. https://www.drugabuse.gov/publications/drugfacts/marijuana-medicine. Apr. 28, 2017. (Year: 2017).*
King, "Pot for Pets: How Medical Marijuana Can Help Your Cat", pp. 1-35, 2015.*
Medical Marijuana Inc News, Top 5 High0CBD and High-THC Cannabis Strains, pp. 1-9, 2017.*
Prisco, "Pot for Pets: Marijuana Cookies for AilingDogs Hit Market", pp. 1-3, 2015.*
International Search Report and Written Opinion for corresponding International Application No. PCT/IB2017/055006, dated Mar. 22, 2018, 6 pages.

* cited by examiner

*Primary Examiner* — Deborah D Carr
(74) *Attorney, Agent, or Firm* — David W. Ladner; Ladner Patent Management LLC

(57) ABSTRACT

Blended, processed marijuana and/or hemp *cannabis* compounds and methods of making the same are provided. In particular, the compound includes one or more species of *cannabis* mixed in various ways with other ingredients in order to produce a new matter, food product, oil, or drink, in the form of gummies, creams, salves, tablets, capsules, pastes, gelatin suppositories, crystals, ointments, jellies, e-juices, powders, pills, syrups, drops, patches, chewing gums, dried whole or partial plant parts, and dusts, such that it is safe for mammals and provides assistance in dealing with various ailments and diseases.

9 Claims, No Drawings

US 10,668,044 B2

BLENDED CANNABIS COMPOUNDS AND METHODS OF MAKING THE SAME

CROSS-REFERENCE TO RELATED APPLICATION

This application claims the benefit of priority to U.S. Application No. 62/525,527 filed on Jun. 27, 2017, the content of which is incorporated herein by reference in its entirety for all purposes.

FIELD

The presently-disclosed invention relates generally to blended/processed *cannabis* compounds, and more particularly to blended hybrid *cannabis* medicaments and methods for making the same.

BACKGROUND

With mounting instances of abuse, addiction, and death caused by anti-psychotic medication, there has been a recent increase in the search for alternative forms of medicating those who need help. Not just in humans, but in other mammals like dogs, a large number of prescription medicines either have terrible side effects or are ineffective for their intended purpose. This expanded search for alternative remedies has led to an increase in the development of *cannabis*-based medications. *Cannabis*, or marijuana, comes in various forms which includes whole and/or partial plants utilization, with some possessing a high psychoactive content and others having no psychoactive effect. Both humans and other mammals have specific cannabinoid receptor sites. These sites are primarily in the brain and central nervous system and in peripheral organs, especially immune cells. Together, the receptors make up what is called the "endocannabinoid system." The molecule that is responsible for most of the psychoactive effects of marijuana is called tetrahydrocannabinol, or THC. This molecule mimics the naturally produced neurotransmitter known as anandamine by stimulating the CB1 receptors in the brain to create the psychoactive, "high" feeling often associated with marijuana. On the other hand, the cannabidiol, or CBD, molecule found in some marijuana actually counteracts the effects of psychoactive molecules like THC. CBD is an antagonist to the CB1 and/or CB2 receptors and opposes the effects of THC. However, THC being psychoactive and CBD being non-psychoactive does not mean that one or the other is bad or good individually. The interactive synergy between *cannabis* compounds has been coined the "entourage effect" and offers a full spectrum of therapeutic compounds (e.g., cannabinoids and terpenoids) from "whole plant medicine.".

In this regard, while there are many possible benefits to marijuana based medicines (which are endocannabinoid enhancers (eCBEs)), to this point in time, there has been difficulty in creating effective hybrid *cannabis* plants that, when mixed them with other substances, create effective medicines with minimal side effects for mammals.

BRIEF SUMMARY

One or more embodiments of the invention may address one or more of the aforementioned problems. Certain embodiments provide compounds and methods for treating various ailments in mammals. In one aspect, a blended and processed *cannabis* compound for treatment of an ailment in a mammal in need thereof is provided. The compound may include a *cannabis* component comprising one or more of *Cannabis sativa, Cannabis indica*, and *Cannabis ruderalis* and at least one additive.

In another aspect, a method of making a blended and processed *cannabis* compound for treatment of an ailment in a mammal in need thereof is provided. The method may include processing a *cannabis* component comprising one or more of *Cannabis sativa, Cannabis indica*, and *Cannabis ruderalis* to form a processed *cannabis* component and combining the processed *cannabis* component with at least one additive.

DETAILED DESCRIPTION

The invention now will be described more fully. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

This invention includes, according to certain embodiments, a matter, substance, compound, material, element, food product, oil, or drink, which contains a hybrid THC/CBD marijuana blend. In particular, embodiments of the invention are directed to the combination of hybrid marijuana strains with various other substances in order to create medical remedies for various illness and pains that transpire in the life cycle of mammals.

I. Definitions

The term "marijuana" may encompass any combination of the three *cannabis* species: *Sativa, Indica*, and *Ruderalis*. Additionally, it will be used interchangeably with *cannabis* in the present specification.

The term "soil" refers to natural soil found in the ground.

The term "engineered soil" refers to synthetic soil manufactured to have specific soil-like qualities referred to as engineered soil in this application. Engineered soil may contain soil in addition to other materials in order to create the desired profile.

The term "species" is relating to the three species subgroups of *cannabis: Sativa, Indica*, and *Ruderalis*. For the purposes of this application, species may be used in reference to hybrids of the above three as well.

The term "THC" refers to the tetrahydrocannabinol molecule found in *cannabis*. It is often related to the psychoactive effects that are associated with *cannabis*. THC may refer to various types of THC, including delta 8 and delta 9. It may also be used interchangeably with THCa in the application.

The term "CBD" refers to the cannabidiol molecule found in *cannabis*. It counteracts the psychoactive effects of THC resulting in less of a "high" in high-CBD *cannabis* than in low-CBD *cannabis*. It may be used interchangeably with CBDa.

The term "CBC" refers to the Cannabichromene molecule found in *cannabis*. This molecule has been shown to have anti-depressant effects.

The term "CBG" refers to the Cannabigerol molecule found in *cannabis*. This molecule is an antagonist to the CB1 receptor and therefore a higher percentage creates less of the "high" effect in *cannabis*.

The term "CBN" refers to the cannabinol molecule found in *cannabis*. It has little to no psychoactive effect and generally exists in small amounts in *cannabis* plants.

The term "CBDV" refers to the Cannabidivarin molecule found in *cannabis*. Similar to CBD, CBDV works as an antagonist to the CB1 receptors in the brain.

The term "CBDa" refers to Cannabidiolic acid in *cannabis*. CBDa can be converted into CBD when it is aged and heated.

The term "delta 9 THC" refers to a specific type of THC that has a higher psychoactive potency than delta 8 THC also found in lesser amounts in *cannabis*.

The term "THCa" refers to the tetrahydrocannabinolic acid found in *cannabis*. THCa is found in living, raw plants and as the plant dries and/or is heated converts to THC.

The term "delta 9 THCa" refers to a specific type of THCa that has a higher psychoactive potency than delta 8 THC, which is also found in lesser quantities in *cannabis* plants.

*Cannabis sativa* ("*Sativa*") is known for its high amount of THC, while only possessing a minimal amount of CBD. As outlined above, THC is the psychoactive component of *Cannabis* and therefore *Sativa* is much more related to the psychoactive or "high" aspects of marijuana than other species. *Sativa* can cause users to be more energetic, sociable, creative, and cheerful.

*Cannabis indica* ("*Indica*"), also has more THC than CBD, but the ratios are closer and is therefore more commonly thought of in the medical marijuana aspect of *cannabis*. Considered by some to be a "nighttime" *cannabis*, *Indica* can cause users to be relaxed, calm, and sleepy.

*Cannabis ruderalis* ("*Ruderalis*") is thought by some to be a subgroup of *Sativa*, but for the purposes of this disclosure, *Sativa* and *Ruderalis* are treated as separate species. *Ruderalis* has a much lower THC amount than the other two plants and therefore does not have a very robust psychoactive "high." It also has a high amount of CBD, which makes it a good match for high THC species when creating hybrids. *Ruderalis* plants are autoflowering, which means they grow according to their maturity, typically 21 to 30 days after a seed is planted, instead of growing in relation to the lighting cycles as *Indica* and *Sativa* both do.

II. Soil and Environment

Certain embodiments may comprise an amalgam of soil with water and light of day. This amalgam also may contain engineered water with a pH level of 5.5 to 7.5. Additionally, an engineered environment may be created to house the amalgam. This engineered environment may be maintained at a temperature of 5 to 35 degrees Celsius. This engineered environment may comprise a humidity from 50% to 65%. This engineered environment may comprise a wind speed from 1 to 7 mph. This engineered environment may comprise a $CO_2$ count of 1100 to 2000 ppm. The engineered environment may include, but is not limited to, any combination of the above temperature, humidity, wind speed, and/or $CO_2$ count. This amalgam may also be subjected to artificial light for 6 to 20 hours per day.

In other embodiments, an amalgam of engineered soil may comprise a pH level of 5.2 to 7.5. This amalgam also may contain engineered water with a pH level of 5.5 to 7.5. Additionally, an engineered environment may be created to house the amalgam. This engineered environment may comprise a temperature of 5 to 35 degrees Celsius. This engineered environment may comprise a humidity from 50% to 65%. This engineered environment may comprise a wind speed from 1 to 5 mph. This engineered environment may comprise a $CO_2$ count of 1100 to 2000 ppm. The engineered environment may include any combination of the above temperature, humidity, wind speed, and/or $CO_2$ count. This amalgam may also be subjected to artificial light for 6 to 20 hours.

In certain embodiments, the engineered soil may contain from 600 to 800 pounds of organic potting soil and/or from 50 to 200 pounds of composted cow manure, which may be added to 50 to 100 pounds of organic worm casting. The engineered soil may also include one or more of the following: 10 pounds steamed bone meal, 10 pounds of bloom bat guano, 10 pounds of blood meal, 3 cups of azomite, 6 pounds of rock phosphate, 1.5 cups of Epson salt, 1 to 2 cups of sweet lime, 2 to 4 tablespoons of powdered humic acid, and/or 6 to 12 gallons of water with a pH level from 5.5 to 7.5. This soil may then be rested in the sun for 35 to 70 days.

III. Marijuana Hybrid

As discussed above, the species of *cannabis* are *Sativa*, *Indica*, and *Ruderalis*. In certain embodiments, a hybrid of *cannabis* species may be used. Additionally, there may additionally be some hybrid marijuana plants that are used to create subsequent, different hybrids.

Combination of *Sativa* and *Indica*

In one embodiment the var cultivar may comprise a hybrid possessing between 0.1 and 99 wt % *Sativa* and between 0.1 and 99 wt % of *Indica*. For example, in one embodiment the hybrid may contain 90 wt % *Sativa* and 10 wt % *Indica*. In another embodiment the hybrid may contain 25 wt % *Sativa* and 75 wt % *Indica*. As *Sativa* has higher THC levels, hybrids with higher *Sativa* ratios would contain a higher percentage of THC than those with higher amounts of *Indica*, which possesses higher levels of CBD. A sample embodiment may have ratios of both *Sativa* and *Indica* that result in an offsetting of the effects of THC and CBD. The resulting hybrid may have a THC level between 0 and 70% and a CBD level between 0 and 70%.

Combination of *Sativa* and *Ruderalis*

In some embodiments, the var cultivar may comprise a hybrid possessing between 0.1 and 99 wt % *Sativa* and between 0.1 and 99 wt % of *Ruderalis*. For example, in one embodiment the hybrid may contain 90 wt % *Sativa* and 10 wt % *Ruderalis*. In another embodiment the hybrid may contain 25 wt % *Sativa* and 75 wt % *Ruderalis*. As *Sativa* has higher THC levels, the hybrids with higher *Sativa* ratios may contain a higher percentage of THC than those with higher ratios of *Ruderalis*, which contains very little THC. A sample embodiment may have a similar ratio of both *Sativa* and *Ruderalis* in order to offset the effects of the other.

Combination of *Indica* and *Ruderalis*

In another embodiment, the var cultivar may comprise a hybrid possessing between 0.1 and 99 wt % *Indica* and between 0.1 and 99 wt % of *Ruderalis*. For example, in one embodiment the hybrid may contain 90 wt % *Ruderalis* and 10 wt % *Indica*. In another embodiment the hybrid may contain 25 wt % *Ruderalis* and 75 wt % *Indica*. As *Indica* only has moderate THC levels and *Ruderalis* has almost none, the hybrids of these two plants will have only a low to moderate amount of THC, while possessing a high CBD percentage.

Combination of All Three Species

In still another embodiment the var cultivar may comprise a hybrid possessing combination of between 0.1 and 99 wt % each of *Indica*, *Ruderalis*, and *Sativa*. For example, in one embodiment the hybrid may contain 70 wt % *Sativa*, 10 wt % *Indica*, and 20 wt % *Ruderalis*. In another embodiment the hybrid may contain 25 wt % *Sativa*, 70 wt % *Indica*, and 5 wt % *Ruderalis*. As *Sativa* has higher THC levels, *Indica* has some THC combined with CBD, and *Ruderalis* has minimal THC with a large amount of CBD, the ratio of THC and CBD may be vastly different based on the percentages of each plant. A sample embodiment may have similar amounts of *Sativa*, *Indica*, and *Ruderalis* in order to offset the effects of each other.

In certain embodiments, the hybrid marijuana may be cultivated by cloning other species or hybrids together.

In other embodiments, the hybrid marijuana may be cultivated using seeds from other hybrid marijuana plants.

In some embodiments, the hybrid marijuana may be created by grafting or propagating multiple strains together. In this embodiment, there may be a "new stock" that is being grafted into a "mother stock." This may be done by taking a very sharp sterilized knife and scraping off the exterior bark of the new stock to expose the inner stem. Once the new stock is exposed, a notch may be cut into the mother plant in order for the new stock to be inserted at an angle between 0 and 90 degrees counterclockwise from the mother stock. After the new stock is inserted, the new stock may be bound to the mother stock using string or adhesives. Additional water may be introduced into the system and then a cling film may be wrapped around the two plants to retain the moisture. There may also be a small amount of growth left just above the incision placement on the mother plant to aid the growing and grafting of the plants.

In another embodiment, the hybrid marijuana may also be created by grafting multiple strains together. In this embodiment, there may be a "new stock" that is being grafted into a "receiving stock." This may be done by taking a very sharp sterilized knife and scraping off the exterior bark of the new stock to expose the inner stem. The receiving plant then may have a V shape cut into the top of one of its stem. The point of the new stock may then be gently pushed into the slot created in the receiving stock. The combined stocks may then be wrapped together to ensure that the two stocks are unlikely to separate. A flexible tie or similar adhesive that does not cut into the stem of either stock and ensures oxygen flow to both may be used to hold the two together initially.

In still another embodiment, the hybrid marijuana may again be created by grafting multiple strains together. In this embodiment, there may be a "new stock" that is being grafted with a "mother stock." This may be done by taking a very sharp sterilized knife and slicing off a thin layer of bark along the stock of two different marijuana species. This may be done using two separate rooted plants or this may also be done by attaching the branch of one plant to the branch of a mother plant. In particular, either stock may be placed together so that the areas without bark are touching each other. The combined stocks may then be wrapped together to ensure that the two stocks are unlikely to separate. A flexible tie or similar adhesive that does not cut into the stem of either stock and ensures oxygen flow to both without breaking the bark may be used to hold the two together initially.

In some embodiments, the hybrid may be some combination of *Indica*, *Sativa*, and *Ruderalis*. This hybrid may be allowed to grow for 1 month to 1 year from the time of planting or grafting and/or propagation. The size of the hybrid may be from 0.1 feet to 15 feet in height. The hybrid may weigh from 0.1 pounds to 500 pounds. This hybrid may be set in different shaped containers including round, square, rectangle, pentagon, or triangle. The container may be made of materials such as glass, plastic, fiberglass, metal, foam, or paper. This container may be from 0.1 inches to 5 feet in width, 0.1 inches to 5 feet in depth, and 0.1 inches to 15 feet in height.

In other embodiments, the hybrid may also be grown in the ground in either soil or engineered soil. It may be allowed to age from 1 month to 1 year from the time of planting. It may be 0.1 to 15 feet in height and have a weight from 0.1 to 500 pounds.

III. Processing of Hybrid Marijuana Plant

In some embodiments, the *cannabis* hybrid used may have a particle size from 0.2 microns to 750 microns. This may be achieved by trimming the *cannabis* for trichrome materials. This may also be achieved by treating the *cannabis* for trichrome materials, lipid-based extracts, and/or synthesized fatty acids of a pharmaceutical composition using one or more of the following: alcohol, carbon dioxide, apple cider vinegar, water, freeze drying, ice water, or steam. The *cannabis* may be screened to remove residue or dregs using screens ranging from course (approximately 1000 microns) to fine (approximately 25 microns).

The hybrid plant may then be ball milled for 0.2 minutes to 6 hours at a temperature of 35 to 140 degrees Celsius until it has a particle size from 0.2 microns to 750 microns. The hybrid plant may also be cut, grated, blended, cooked, crunched, baked, compressed, pulverized, crushed, pressed, triturated, or grinded in order to achieve a particle size from 0.2 microns to 750 microns in size at a temperature from 35 to 140 degrees Celsius. The hybrid may also be converted to a gas or liquid as required for the targeted medical use. All of these actions may be performed on the hybrid plant before it is combined with other ingredients. All of these actions may also be performed on the hybrid plant after it is combined with other ingredients. Additionally, all of these actions may be performed both before and after the hybrid plant is combined with other ingredients.

IV. Combination of Marijuana Hybrid With Other Ingredients

After the hybrid grows and is processed, it may be combined with other substances in order to produce a new substance, matter, compound, material, element, oil, or drink. This combination may be achieved by one or more of the following: cutting, grating, blending, cooking, crunching, brewing, compressing, milling, pulverize, crush, pressing, baking, triturate/trituration, crushing, grinding and mixing of various particle size and/or liquefied to achieve a blended *cannabis* compound.

Embodiments of the invention may combine the marijuana hybrid with various other compounds having both pharmaceutical and non-pharmaceutical elements, substances, materials and compounds including but not limited to sterols, triglycerides, alkanes, myrcene, limonene, alpha-pinene, beta-pinene, linalool, beta-caryophyllene, beta-ocimene, caryophyllene oxide, caryophyllene, terpinolene tinctures, terpene oil, humulene, *cannabis* plant waxes, omega-3 fatty acids, various plant oils (e.g., olive oil), alkanes, nitrogenous compounds, sugars, omega-6 fatty acids, amino acids (e.g., leucine, isoleucine, lysine, methionine, phenylalanine, threonine, tryptophan, valine, histidine), aldehydes, lecithin, flour, omega-9 fatty acids, chromium picolinate, herbs, ketones, chocolate, pectin, flavonoids, glycosides, shortening, methylsulfonylmethane, coffee, spices, calcium ascorbate, vanilla, manganese proteinate, potassium bicarbonate, potassium sulfate, vitamin A, vitamin B-12, vitamin C, vitamin E, riboflavin, honey, glucosamine, eggs, chondroitin, maple syrup, carprofen (i.e. Rimadyl™), pigments, milk, butter, or water. In certain embodiments, water may comprise a pH level of 6.0 to 7.0. In some embodiments, the resulting blended *cannabis* compound may comprise a food product, an oil, or a drink for mammals, including, by way of example only, humans, canines, felines, and/or the like.

In some embodiments, the blended *cannabis* compounds may be configured to treat a variety of ailments including, but not limited to, acquired hypothyroidism, acute gastritis, agoraphobia, AIDS related illness, alcohol abuse, alcoholism, alopecia areata, Alzheimer's disease, amphetamine dependency, amyloidosis, amyotrophic lateral sclerosis (ALS), angina pectoris, ankylosis, anorexia, anorexia nervosa, anxiety disorders, any chronic medical symptom that limits major life activities, arteriosclerotic heart disease, arthritis, rheumatoid arthritis, arthropathy, gout, asthma, attention deficit hyperactivity disorder (ADHD), autism, Asperger's, autoimmune disease, back pain, back sprain, Bell's palsy, bipolar disorder, malignant brain tumor, bruxism, bulimia, cachexia, cancer, carpal tunnel syndrome, cerebral palsy, cervical disk disease, cervicobrachial syndrome, chemotherapy, chronic fatigue syndrome, chronic pain, chronic renal failure, cocaine dependence, colitis, conjunctivitis, constipation, Crohn's disease, cystic fibrosis, damage to spinal cord nervous tissue, Darier's disease, degenerative arthritis, degenerative arthropathy, delirium tremens, dermatomyositis, diabetes, diabetic neuropathy, diabetic peripheral vascular disease, diarrhea, diverticulitis, dysthymic disorder, eczema, emphysema, endometriosis, epidermolysis bullosa, epididymitis, epilepsy, Felty's syndrome, fibromyalgia, Friedreich's ataxia, gastritis, genital herpes, glaucoma, glioblastoma multiforme, Graves' disease, cluster headaches, migraine headaches, tension headaches, hemophilia A, Henoch-Schonlein purpura, hepatitis C, hereditary spinal ataxia, HIV/AIDS, Huntington's disease, hypertension, hyperventilation, hypoglycemia, impotence, inflammatory autoimmune-mediated arthritis, inflammatory bowel disease (IBD), insomnia, intermittent explosive disorder (IED), intractable pain, intractable vomiting, lipomatosis, Lou Gehrig's disease, Lyme's disease, lymphoma, major depression, melanoma, mania, melorheostosis, Meniere's disease, motion sickness, mucopolysaccharidosis (MPS), multiple sclerosis (MS), muscle spasms, muscular dystrophy, myeloid leukemia, Nail-Patella syndrome, nightmares, obesity, obsessive compulsive disorder, opiate dependence, osteoarthritis, panic disorder, Parkinson's disease, peripheral neuropathy, peritoneal pain, persistent insomnia, porphyria, post-polio syndrome (PPS), post-traumatic arthritis, post-traumatic stress disorder (PTSD), premenstrual syndrome (PMS), prostatitis, psoriasis, pulmonary fibrosis, quadriplegia, radiation therapy, Raynaud's disease, Reiter's syndrome, restless legs syndrome (RLS), rheumatoid arthritis, rosacea, schizoaffective disorder, schizophrenia, scoliosis, sedative dependence, seizures, senile dementia, severe nausea, shingles (herpes zoster), sinusitis, skeletal muscular spasticity, sleep apnea, sleep disorders, spasticity, spinal stenosis, Sturge-Weber syndrome (SWS), stuttering, tardive dyskinesia (TD), temporomandibular joint disorder (TMJ), tenosynovitis, terminal illness, thyroiditis, tic douloureux, Tietze's syndrome, tinnitus, tobacco dependence, Tourette's syndrome, trichotillomania, viral hepatitis, wasting syndrome, whiplash, Wittmaack-Ekbom's syndrome, writers' cramp, nausea, vomiting, premenstrual syndrome, unintentional weight loss, lack of appetite, spasticity, painful conditions, especially neurogenic pain, movement disorders, asthma, glaucoma, adrenal disease, and related conditions.

In some embodiments, the ingredients may be cooked. In such embodiments, the cooking may take place using, for example, a gas burner, hot plate, slow cooker, and/or the like. In certain embodiments, the temperature during cooking may be from about 1 to about 250 degrees Celsius (e.g., about 177 degrees Celsius). In further embodiments, cooking may occur for a duration of about 1 minute to about 72 hours total (e.g., 1 hour).

In still other embodiments, the ingredients may be baked. In such embodiments, the baking may take place in an oven. In certain embodiments, the blend may be baked from about 1 minute to about 48 hours. In further embodiments, for example, the blend may be baked for about 30 to 60 minutes. The blend may be baked at a temperature from about 35 to about 500 degrees Celsius (e.g., about 177 degrees Celsius).

In other embodiments, the ingredients may be brewed. The ingredients may be brewed using water. In some embodiments, the water may be at a temperature from about 1 to about 145 degrees Celsius (e.g., about 78 degrees Celsius). In further embodiments, the brewing may occur from about 20 minutes to about 250 minutes total. The brewing may occur for about 90 minutes.

In certain embodiments, the ingredients may be compressed. In some embodiments, the compression may occur via a machine or by hand. The amount of compression could be from about 0.25 pounds to about 5 tons (e.g., about 2 tons).

In other embodiments, the ingredients may be milled to achieve a particle size from about 0.2 microns to about 750 microns (e.g., about 100 microns).

EXAMPLES

The following examples are provided for illustrating one or more embodiments of the present invention and should not be construed as limiting the invention.

Example 1

In one example embodiment, the marijuana may be a hybrid or clone of two or more of the following: *Sativa, Indica,* and *Ruderalis*. This hybrid may have a CBD level of 8% to 26%. Additionally, it may have a CBG level of 4% to 10%. The CBN level may be 5% to 12%. The CBDV level may be 5% to 20%. This hybrid may also have a THC level of 2% or less. The embodiment may comprise about 10 mg (or more) of this hybrid. It may also comprise, but is not limited to, from about 575 to about 725 mg of Glucosamine HCL. It may also be combined with 75 to 130 mg of Chondroitin sulfate. Additionally, 40 to 60 mg of Calcium ascorbate may be added. This Calcium ascorbate may be one or both of Omega-3 or Omega-6. There may also be 3 to 9 mg of Manganese proteinase. Additionally, there may be Vitamin E added, as well as one or more of the following: wheat flour, corn syrup, sugar, beef, salt, glycerin, crystalline fructose, water, dried cheese product, soy protein concentrate, citric acid, vegetable oil, garlic power, caramel color, onion extract, or natural smoke flavor. This embodiment may be combined by milling, pulverizing, crushing, grinding, pressing, extruding, or triturating. This embodiment may be used for hip, joint, and bone maintenance for mammals.

Example 2

In another embodiment, the marijuana may be a hybrid or clone of two or more of the following: *Sativa, Indica*, and *Ruderalis*. This hybrid may contain 10% to 24% CBD. It may also contain 5% to 14% CBC. The hybrid may contain 10% to 20% CBN. It may comprise 4% to 20% THC. This may be Delta 9 THC. This THC level may be achieved by blending, mixing, grinding, liquefying, or milling. The embodiment may contain, but is not limited to, about 1 g of the *cannabis* hybrid. Additionally, the *cannabis* may be combined with amino acids, such as 1 to 7 grams of leucine, 2 to 5 grams of isoleucine, 1 to 3 grams of lysine, 80 mg of methionine, 350 to 500 mg of L-phenylalanine, 2 to 4 grams of L-tryptophan, 3 to 6 grams of valine, 400 mg of histidine, or 100 to 500 mg of threonine. The embodiment may be mixed with one or more of the following: iron, zinc, manganese, phosphorus, iodine, calcium, riboflavin, selenium, chromium, calcium, thiamin, niacin, biotin, selenium, copper, molybdenum, folic acid, pantothenic acid, vitamin A, vitamin B6, vitamin B12, vitamin C, vitamin D, vitamin E, riboflavin, vitamin K, 5 to 18 ounces of condensed milk or ice cream, omega-3 fatty acid, omega-6 fatty acid, ibuprofen, thiamin, biotin, sugar, molybdenum, folic acid, vanilla, pantothenic acid, 4 to 12 tablespoons of coffee, aspirin, soda water, bupropion, acetaminophen, or lorazepam.

Example 3

In still another embodiment, the marijuana may be a hybrid or clone of two or more of the following: *Sativa, Indica*, and *Ruderalis*. This marijuana hybrid may contain 8% to 24% CBD, 5% to 10% CBC, 5% to 10% CBG, 5 to 10% CBDa, 5% to 25% THC, and 5% to 20% THCa. The THC and THCa may be delta 9. This THC level could be achieved by blending, mixing, grinding, liquefying, or milling. The embodiment may contain, but is not limited to, about 1 g of the *cannabis* hybrid. Additionally, the *cannabis* may be combined with amino acids, such as 1 to 7 grams of leucine, 2 to 5 grams of isoleucine, 1 to 3 grams of lysine, 80 mg of methionine, 350 to 500 mg of L-phenylalanine, 2 to 4 grams of L-tryptophan, 3 to 6 grams of valine, 400 mg of histidine, or 100 to 500 mg of threonine. The embodiment may be mixed with one or more of the following: iron, zinc, manganese, phosphorus, iodine, calcium, riboflavin, selenium, chromium, calcium, thiamin, niacin, biotin, selenium, copper, molybdenum, folic acid, pantothenic acid, vitamin A, vitamin B6, vitamin B12, vitamin C, vitamin D, vitamin E, or vitamin K, 5 to 12 ounces of condensed milk, omega-3 fatty acid, omega-6 fatty acid, ibuprofen, thiamin, biotin, sugar, molybdenum, folic acid, pantothenic acid, 4 to 12 tablespoons of coffee, aspirin, bupropion, acetaminophen, or lorazepam.

Example 4

In another embodiment, the marijuana may be a hybrid or clone of two or more of the following: *Sativa, Indica*, and *Ruderalis*. This marijuana hybrid may contain 2% to 24% CBD, 0% to 12% CBC, 5% to 10% CBG, 5% to 15% CBDV, 5% to 18% THC, and 5% to 12% THCa. The THC and THCa may be delta 9. This THC level may be achieved by blending, mixing, grinding, liquefying, or milling. The embodiment may contain, but not limited to, about 1 g of the *cannabis* hybrid. Additionally, the *cannabis* may be combined with amino acids, such as 1 to 7 grams of leucine, 2 to 5 grams of isoleucine, 1 to 3 grams of lysine, 80 mg of methionine, 350 to 500 mg of L-phenylalanine, 2 to 4 grams of L-tryptophan, 3 to 6 grams of valine, 400 mg of histidine, or 100 to 500 mg of threonine. The embodiment may be mixed with one or more of the following: iron, zinc, manganese, phosphorus, iodine, calcium, riboflavin, selenium, chromium, thiamin, niacin, biotin, copper, molybdenum, folic acid, pantothenic acid, vitamin A, vitamin B6, vitamin B12, vitamin C, vitamin D, vitamin E, or vitamin K, coconut milk, omega-3 fatty acid, omega-6 fatty acid, SAMe, limbrel, resveratrol, boswellic acid, curcumin, histamine dihydrochioride (0.025%), emu oil, methyl sulfonylmethane, C 13-14, isoparaffin, polyacrylamide, trideceth-6, methylisothiazolinone, potassium sorbate, tetrasodium EDTA, laureth-7, butylene glycol, sunflower oil, methyisulfonylamide, deionized water, ibuprofen, glucosamine, chondroitin, thiamin, biotin, molybdenum, folic acid, pantothenic acid, aspirin, bupropion, acetaminophen, or lorazepam.

Example 5

In a different embodiment, the marijuana may be a hybrid or clone of two or more of the following: *Sativa, Indica*, and *Ruderalis*. This marijuana hybrid may contain 5% to 16% CBC, 4% to 14% CBC, 5% to 10% CBN, and 1% to 8% THC. This embodiment may be achieved by blending, mixing, grinding, liquefying, or milling about 1 g of *cannabis* hybrid with amino acids, such as 1 to 7 grams of leucine, 2 to 5 grams of isoleucine, 1 to 3 grams of lysine, 80 mg of methionine, 350 to 500 mg of L-phenylalanine, 2 to 4 grams of L-tryptophan, 3 to 6 grams of valine, 400 mg of histidine, or 100 to 500 mg of threonine. The embodiment may be mixed with one or more of the following, but is not limited to: iron, zinc, manganese, phosphorus, iodine, calcium, riboflavin, selenium, chromium, thiamin, niacin, biotin, copper, molybdenum, folic acid, pantothenic acid, vitamin A, vitamin B6, vitamin B12, vitamin C, vitamin D, vitamin E, or vitamin K, 5 to 12 ounces of condensed milk, omega-3, omega-6 fatty acid, vanilla, SAMe, limbrel, resveratrol, boswellic acid, curcumin, histamine dihydrochioride (0.025%), emu oil, methylsulfonylmethane, C 13-14, isoparaffin, polyacrylamide, trideceth-6, methylisothiazolinone, potassium sorbate, tetrasodium EDTA, laureth-7, butylene glycol, sunflower oil, methyisulfonylamide, deionized water, ibuprofen, glucosamine, chondroitin, thiamin, biotin, molybdenum, folic acid, pantothenic acid, aspirin, bupropion, acetaminophen, or lorazepam.

Example 6

In some embodiments, the marijuana may be a hybrid or clone of two or more of the following: *Sativa, Indica*, and *Ruderalis*. This marijuana hybrid may contain 5% to 16% CBD, 4% to 14% CBC, 5% to 10% CBN, and 1% to 8% THC. This embodiment may be achieved by blending, mixing, grinding, liquefying, or milling about 1 g of *cannabis* hybrid with amino acids, such as 1 to 7 grams of leucine, 2 to 5 grams of isoleucine, 1 to 3 grams of lysine, 80 mg of methionine, 350 to 500 mg of L-phenylalanine, 2 to 4 grams of L-tryptophan, 3 to 6 grams of valine, 400 mg of histidine, or 100 to 500 mg of threonine. The embodiment may be mixed with one or more of the following but is not limited to: iron, zinc, manganese, phosphorus, iodine, calcium, riboflavin, selenium, chromium, thiamin, niacin, biotin, copper, molybdenum, folic acid, pantothenic acid, vitamin A, vitamin B6, vitamin B12, vitamin C, vitamin D, vitamin E, or vitamin K, 5 to 12 ounces of condensed milk, omega-3 fatty acid, omega-6 fatty acid, omega-9 fatty acid, vanilla, SAMe, limbrel, resveratrol, boswellic acid, curcumin, histamine dihydrochioride (0.025%), emu oil, methylsulfonylmethane, C 13-14, isoparaffin, polyacrylamide, trideceth-6, methylisothiazolinone, potassium sorbate, tetrasodium EDTA, laureth-7, butylene glycol, sunflower oil, methyisulfonylamide, deionized water, ibuprofen, glucosamine, chondroitin, thiamin, biotin, molybdenum, folic acid, pantothenic acid, aspirin, bupropion, acetaminophen, or lorazepam.

Example 7

In still another embodiment, the marijuana may be a hybrid or clone of two or more of the following: *Sativa*, *Indica*, and *Ruderalis*. This marijuana hybrid may contain 10% to 24% CBD, 2% to 8% CBN, and 10% to 24% THC. This embodiment may be achieved by blending, mixing, grinding, liquefying, or milling about 1 g of *cannabis* hybrid with amino acids, such as 1 to 7 grams of leucine, 2 to 5 grams of isoleucine, 1 to 3 grams of lysine, 80 mg of methionine, 350 to 500 mg of L-phenylalanine, 2 to 4 grams of L-tryptophan, 3 to 6 grams of valine, 400 mg of histidine, or 100 to 500 mg of threonine. This embodiment may also be combined, but is not limited to, with 1200 mg of lipoic Acid, 500 mg of Coenzyme Q 10, and/or one or more of the following: 1 cup of shortening or lard, 2 eggs, brown sugar, vanilla, 3 cups of wheat or rice flour, soda, salt, or peanut butter. This may be baked for about 10 minutes at an oven temperature of 177 degrees Celsius.

Non-Limiting Exemplary Embodiments

Having described various aspects and embodiments of the invention herein, further specific embodiments of the invention include those set forth in the following paragraphs.

In one aspect, a blended and processed *cannabis* compound for treatment of an ailment in a mammal in need thereof is provided. The compound may include a *cannabis* component comprising one or more of *Cannabis sativa*, *Cannabis indica*, and *Cannabis ruderalis* and at least one additive. In some embodiments, for example, the *cannabis* component may comprise a hybrid of at least two of *Cannabis sativa*, *Cannabis indica*, and *Cannabis ruderalis*. In further embodiments, for instance, the *cannabis* component may comprise from about 0 to about 70% tetrahydrocannabinol (THC) and from about 0 to about 70% cannabidiol (CBD). In some embodiments, for example, the mammal comprises a human, a canine, or a feline.

According to certain embodiments, for example, the *cannabis* component may comprise from about 0.1 to about 99 wt % *Cannabis sativa* and from about 0.1 to about 99 wt % *Cannabis indica*. In other embodiments, for instance, the *cannabis* component may comprise from about 0.1 to about 99 wt % *Cannabis sativa* and from about 0.1 to about 99 wt % *Cannabis ruderalis*. In further embodiments, for example, the *cannabis* component may comprise from about 0.1 to about 99 wt % *Cannabis indica* and from about 0.1 to about 99 wt % *Cannabis ruderalis*. In some embodiments, for instance, the *cannabis* component may comprise from about 0.1 to about 99 wt % of each of *Cannabis sativa*, *Cannabis indica*, and *Cannabis ruderalis*.

In accordance with certain embodiments, for example, the additive may comprise at least one of a sterol, a triglyceride, an alkane, myrcene, limonene, alpha-pinene, beta-pinene, linalool, beta-caryophyllene, beta-ocimene, caryophyllene oxide, caryophyllene, a terpinolene tincture, terpene oil, humulene, a *cannabis* plant wax, an omega-3 fatty acid, a plant oil, a nitrogenous compound, a sugar, an omega-6 fatty acid, an amino acid, an aldehyde, lecithin, flour, chromium picolinate, an herb, a ketone, chocolate, pectin, a flavonoid, a glycoside, shortening, methylsulfonylmethane, coffee, a spice, calcium ascorbate, vanilla, manganese proteinate, potassium bicarbonate, potassium sulfate, vitamin A, vitamin B-12, vitamin C, vitamin E, riboflavin, honey, glucosamine, egg, chondroitin, maple syrup, carprofen, a pigment, milk, butter, water, or any combination thereof.

According to certain embodiments, for instance, the ailment may comprise at least one of acquired hypothyroidism, acute gastritis, agoraphobia, AIDS-related illness, alcohol abuse, alcoholism, alopecia areata, Alzheimer's disease, amphetamine dependency, amyloidosis, amyotrophic lateral sclerosis (ALS), angina pectoris, ankylosis, anorexia, anxiety, arteriosclerotic heart disease, arthritis, rheumatoid arthritis, arthropathy, gout, asthma, attention deficit hyperactivity disorder (ADHD), autism, Asperger's, autoimmune disease, back pain, back sprain, Bell's palsy, bipolar disorder, bruxism, bulimia, cachexia, cancer, carpal tunnel syndrome, cerebral palsy, cervical disk disease, cervicobrachial syndrome, chemotherapy, chronic fatigue syndrome, chronic pain, chronic renal failure, cocaine dependence, colitis, conjunctivitis, constipation, Crohn's disease, cystic fibrosis, damage to spinal cord nervous tissue, Darier's disease, degenerative arthritis, degenerative arthropathy, delirium tremens, dermatomyositis, diabetes, diabetic neuropathy, diabetic peripheral vascular disease, diarrhea, diverticulitis, dysthymic disorder, eczema, emphysema, endometriosis, epidermolysis bullosa, epididymitis, epilepsy, Felty's syndrome, fibromyalgia, Friedreich's ataxia, gastritis, genital herpes, glaucoma, glioblastoma multiforme, Graves' disease, cluster headaches, migraine headaches, tension headaches, hemophilia A, Henoch-Schonlein purpura, hepatitis C, hereditary spinal ataxia, HIV/AIDS, Huntington's disease, hypertension, hyperventilation, hypoglycemia, impotence, inflammatory autoimmune-mediated arthritis, inflammatory bowel disease (IBD), insomnia, intermittent explosive disorder (IED), intractable pain, lipomatosis, Lou Gehrig's disease, Lyme's disease, lymphoma, major depression, melanoma, mania, melorheostosis, Meniere's disease, motion sickness, mucopolysaccharidosis (MPS), multiple sclerosis (MS), muscle spasms, muscular dystrophy, myeloid leukemia, Nail-Patella syndrome, nightmares, obesity, obsessive compulsive disorder, opiate dependence, osteoarthritis, panic disorder, Parkinson's disease, peripheral neuropathy, peritoneal pain, persistent insomnia, porphyria, post-polio syndrome (PPS), post-traumatic arthritis, post-traumatic stress disorder (PTSD), premenstrual syndrome (PMS), prostatitis, psoriasis, pulmonary fibrosis, quadriplegia, radiation therapy, Raynaud's disease, Reiter's syndrome, restless legs syndrome (RLS), rheumatoid arthritis, rosacea, schizoaffective disorder, schizophrenia, scoliosis, sedative dependence, seizures, senile dementia, shingles (herpes zoster), sinusitis, skeletal muscular spasticity, sleep apnea, sleep disorders, spasticity, spinal stenosis, Sturge-Weber syndrome (SWS), stuttering, tardive dyskinesia (TD), temporomandibular joint disorder (TMJ), tenosynovitis, terminal illness, thyroiditis, tic douloureux, Tietze's syndrome, tinnitus, tobacco dependence, Tourette's syndrome, trichotillomania, viral hepatitis, wasting syndrome, whiplash, Wittmaack-Ekbom's syndrome, writers' cramp, nausea, vomiting, premenstrual syndrome, unintentional weight loss, lack of appetite, neurogenic pain, a movement disorder, asthma, glaucoma, adrenal disease, or any combination thereof.

In another aspect, a method of making a blended and processed *cannabis* compound for treatment of an ailment in a mammal in need thereof is provided. The method may include processing a *cannabis* component comprising one or more of *Cannabis sativa, Cannabis indica*, and *Cannabis ruderalis* to form a processed *cannabis* component and combining the processed *cannabis* component with at least one additive. In some embodiments, for example, processing the *cannabis* component may comprise forming a hybrid of at least two of *Cannabis sativa, Cannabis indica*, and *Cannabis ruderalis*. In further embodiments, for instance, combining the processed *cannabis* component with at least one additive may comprise at least one of ball milling, cutting, grating, blending, cooking, crunching, baking, compressing, pulverizing, carbon dioxide extraction, ether extraction, crushing, pressing, trituration, liquefaction, mixing, grinding, or any combination thereof.

According to certain embodiments, for example, the *cannabis* component may comprise from about 0.1 to about 99 wt % *Cannabis sativa* and from about 0.1 to about 99 wt % *Cannabis indica*. In other embodiments, for instance, the *cannabis* component may comprise from about 0.1 to about 99 wt % *Cannabis sativa* and from about 0.1 to about 99 wt % *Cannabis ruderalis*. In further embodiments, for example, the *cannabis* component may comprise from about 0.1 to about 99 wt % *Cannabis indica* and from about 0.1 to about 99 wt % *Cannabis ruderalis*. In some embodiments, for instance, the *cannabis* component may comprise from about 0.1 to about 99 wt % of each of *Cannabis sativa, Cannabis indica*, and *Cannabis ruderalis*.

In accordance with certain embodiments, for example, the additive may comprise at least one of a sterol, a triglyceride, an alkane, myrcene, limonene, alpha-pinene, beta-pinene, linalool, beta-caryophyllene, beta-ocimene, caryophyllene oxide, caryophyllene, a terpinolene tincture, terpene oil, humulene, a *cannabis* plant wax, an omega-3 fatty acid, a plant oil, a nitrogenous compound, a sugar, an omega-6 fatty acid, an amino acid, an aldehyde, lecithin, flour, chromium picolinate, an herb, a ketone, chocolate, pectin, a flavonoid, a glycoside, shortening, methylsulfonylmethane, coffee, a spice, calcium ascorbate, vanilla, manganese proteinate, potassium bicarbonate, potassium sulfate, vitamin A, vitamin B-12, vitamin C, vitamin E, riboflavin, honey, glucosamine, egg, chondroitin, maple syrup, carprofen, a pigment, milk, butter, water, or any combination thereof.

According to certain embodiments, for instance, the ailment may comprise at least one of acquired hypothyroidism, acute gastritis, agoraphobia, AIDS-related illness, alcohol abuse, alcoholism, alopecia areata, Alzheimer's disease, amphetamine dependency, amyloidosis, amyotrophic lateral sclerosis (ALS), angina pectoris, ankylosis, anorexia, anxiety, arteriosclerotic heart disease, arthritis, rheumatoid arthritis, arthropathy, gout, asthma, attention deficit hyperactivity disorder (ADHD), autism, Asperger's, autoimmune disease, back pain, back sprain, Bell's palsy, bipolar disorder, bruxism, bulimia, cachexia, cancer, carpal tunnel syndrome, cerebral palsy, cervical disk disease, cervicobrachial syndrome, chemotherapy, chronic fatigue syndrome, chronic pain, chronic renal failure, cocaine dependence, colitis, conjunctivitis, constipation, Crohn's disease, cystic fibrosis, damage to spinal cord nervous tissue, Darier's disease, degenerative arthritis, degenerative arthropathy, delirium tremens, dermatomyositis, diabetes, diabetic neuropathy, diabetic peripheral vascular disease, diarrhea, diverticulitis, dysthymic disorder, eczema, emphysema, endometriosis, epidermolysis bullosa, epididymitis, epilepsy, Felty's syndrome, fibromyalgia, Friedreich's ataxia, gastritis, genital herpes, glaucoma, glioblastoma multiforme, Graves' disease, cluster headaches, migraine headaches, tension headaches, hemophilia A, Henoch-Schonlein purpura, hepatitis C, hereditary spinal ataxia, HIV/AIDS, Huntington's disease, hypertension, hyperventilation, hypoglycemia, impotence, inflammatory autoimmune-mediated arthritis, inflammatory bowel disease (IBD), insomnia, intermittent explosive disorder (IED), intractable pain, lipomatosis, Lou Gehrig's disease, Lyme's disease, lymphoma, major depression, melanoma, mania, melorheostosis, Meniere's disease, motion sickness, mucopolysaccharidosis (MPS), multiple sclerosis (MS), muscle spasms, muscular dystrophy, myeloid leukemia, Nail-Patella syndrome, nightmares, obesity, obsessive compulsive disorder, opiate dependence, osteoarthritis, panic disorder, Parkinson's disease, peripheral neuropathy, peritoneal pain, persistent insomnia, porphyria, post-polio syndrome (PPS), post-traumatic arthritis, post-traumatic stress disorder (PTSD), premenstrual syndrome (PMS), prostatitis, psoriasis, pulmonary fibrosis, quadriplegia, radiation therapy, Raynaud's disease, Reiter's syndrome, restless legs syndrome (RLS), rheumatoid arthritis, rosacea, schizoaffective disorder, schizophrenia, scoliosis, sedative dependence, seizures, senile dementia, shingles (herpes zoster), sinusitis, skeletal muscular spasticity, sleep apnea, sleep disorders, spasticity, spinal stenosis, Sturge-Weber syndrome (SWS), stuttering, tardive dyskinesia (TD), temporomandibular joint disorder (TMJ), tenosynovitis, terminal illness, thyroiditis, tic douloureux, Tietze's syndrome, tinnitus, tobacco dependence, Tourette's syndrome, trichotillomania, viral hepatitis, wasting syndrome, whiplash, Wittmaack-Ekbom's syndrome, writers' cramp, nausea, vomiting, premenstrual syndrome, unintentional weight loss, lack of appetite, neurogenic pain, a movement disorder, asthma, glaucoma, adrenal disease, or any combination thereof.

Modifications of the invention set forth herein will come to mind to one skilled in the art to which the invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A drink or food product composition comprising
    a mixture of cannabinoids comprising from 8% to 24% Cannabidiol (CBD), 5% to 10% Cannabichromene (CBC), 5% to 10% Cannabigerol (CBG), 5 to 10% Cannabidiolic acid (CBDa), 5% to 25% Tetrahydrocannabinol (THC), and 5% to 20% Tetrahydrocannabinolic acid (THCa);
    one or more amino acids, selected from leucine, isoleucine, lysine, methionine, L-phenylalanine, L-tryptophan, valine, histidine, and threonine;
    one or more vitamins and minerals selected from iron, zinc, manganese, phosphorus, iodine, calcium, selenium, chromium, calcium, riboflavin, thiamin, niacin, biotin, selenium, copper, molybdenum, folic acid, pantothenic acid, vitamin A, vitamin $B_6$, vitamin $B_{12}$, vitamin C, vitamin D, vitamin E, and vitamin K; and
    one or more nutritional additives and/or flavor enhancers selected from condensed milk, omega-3 fatty acid, omega-6 fatty acid, sugar, instant coffee, dark corn syrup, vanilla, club soda water, and sugar.

2. The composition of claim 1 further comprising one or more medicaments selected from ibuprofen, aspirin, bupropion, acetaminophen, and lorazepam.

3. A food product composition comprising
a mixture of cannabinoids comprising from 8% to 26% Cannabidiol (CBD), 4 to 10% Cannabigerol (CBG), 5 to 12% Cannabinol (CBN), 5% to 20% Cannabidivarin (CBDV), and less than 2% Tetrahydrocannabinol (THC); and
one or more additives selected from Glucosamine HCl, MSM, Chondroitin sulfate, Calcium ascorbate and Manganese proteinase, and Vitamin E.

4. The composition of claim 3 further comprising wheat flour, corn syrup, sugar, beef, salt, glycerin, crystalline fructose, water, dried cheese product, soy protein concentrate, citric acid, vegetable oil, garlic power, caramel color, onion extract, natural smoke flavor.

5. The composition of claim 4 in which the food product is a canine or feline food product.

6. A topically appliable composition comprising
a mixture of cannabinoids comprising from 2% to 24% Cannabidiol (CBD), 0% to 12% Cannabichromene (CBC), 5% to 10% Cannabigerol (CBG), 5% to 15% Cannabidivarin (CBDV), 5% to 18% Tetrahydrocannabinol (THC) and 5% to 12% Tetrahydrocannabinolic acid (THCa);
one or more amino acids, selected from leucine, isoleucine, lysine, methionine, L-phenylalanine, L-tryptophan, valine, histidine, and threonine;
one or more vitamins or minerals selected from iron, zinc, manganese, phosphorus, iodine, calcium, selenium, chromium, calcium, riboflavin, thiamin, niacin, biotin, selenium, copper, molybdenum, folic acid, pantothenic acid, vitamin A, vitamin $B_6$, vitamin $B_{12}$, vitamin C, vitamin D, vitamin E, or vitamin K; and
one or more additional additives selected from coconut milk, omega-3 fatty acid, omega-6 fatty acid, SAMe, limbrel, resveratrol, boswellic acid, curcumin, histamine dihydrochloride (0.025%), emu oil, methyl sulfonyl methane, C 13-14, isoparaffin, polyacrylamide, trideceth-6, methylisothiazolinone, potassium sorbate, tetrasodium EDTA, laureth-7, butylene glycol, sunflower oil, methyl sulfonyl amide, and deionized water.

7. The composition of claim 6 further comprising one or more medicaments selected from glucosamine, chondroitin, ibuprofen, aspirin, bupropion, acetaminophen, and lorazepam.

8. The composition of claim 6 wherein said composition is a cream, salve or ointment.

9. The composition of claim 7 wherein said composition is a cream, salve or ointment.

* * * * *